United States Patent [19]

Kumar et al.

[11] Patent Number: 5,908,755
[45] Date of Patent: Jun. 1, 1999

[54] SEQUENTIAL STEP METHOD FOR SEQUENCING AND IDENTIFYING POLYNUCLEOTIDES

[75] Inventors: Rajan Kumar, Robbinsville; Paul Heaney, Plainsboro, both of N.J.

[73] Assignee: Sarnoff Corporation, Princeton, N.J.

[21] Appl. No.: 08/950,709

[22] Filed: Oct. 15, 1997

Related U.S. Application Data

[63] Continuation of application No. 08/665,210, Jun. 14, 1996, abandoned.

[51] Int. Cl.$^6$ .............. C12Q 1/68; C12P 19/34; G01N 33/48
[52] U.S. Cl. .............. 435/6; 435/91.1; 435/91.2; 436/94
[58] Field of Search .............. 435/6, 91.1, 91.2; 436/94

[56] References Cited

U.S. PATENT DOCUMENTS

| | | | |
|---|---|---|---|
| 4,863,849 | 9/1989 | Melamede | 435/6 |
| 5,002,867 | 3/1991 | Macevicz | 435/6 |
| 5,143,854 | 9/1992 | Pirrung et al. | 436/518 |
| 5,332,666 | 7/1994 | Prober et al. | 435/91.5 |
| 5,334,501 | 8/1994 | Adams et al. | 435/6 |
| 5,359,115 | 10/1994 | Campbell et al. | 558/110 |
| 5,374,524 | 12/1994 | Miller | 435/6 |
| 5,403,708 | 4/1995 | Brennan et al. | 435/6 |
| 5,420,328 | 5/1995 | Campbell | 558/110 |
| 5,424,186 | 6/1995 | Fodor et al. | 435/6 |
| 5,508,164 | 4/1996 | Kausch et al. | 435/6 |
| 5,695,926 | 12/1997 | Cros et al. | 435/5 |

FOREIGN PATENT DOCUMENTS

| | | |
|---|---|---|
| 0 223 618 | 5/1987 | European Pat. Off. . |
| WO 90/13666 | 11/1990 | WIPO ............ C12Q 1/68 |
| WO 92/10092 | 6/1992 | WIPO . |
| WO 93/06121 | 4/1993 | WIPO . |

OTHER PUBLICATIONS

Stallard et al., Anal. Biochem., 162, 197–201 (1987).
Thomas et al., Nucleic Acids Res., 21, 3915–3916 (1993).
Khurana et al. (1994) Hum. Mol. Genet. 3:841.
Borodovsky et al. (1994) Nucl. Acids Res. 22:4756–67.

*Primary Examiner*—Kenneth R. Horlick
*Attorney, Agent, or Firm*—William J. Burke

[57] ABSTRACT

In one aspect, described are methods of sequencing of polynucleotides using a sequential step procedure. The methods of the invention begin with the provision of a single-stranded polynucleotide template that is annealed with a primer, forming a template-primer complex. The methods of the invention can provide for adding discrete nucleotides by a polymerase to the template-primer complex, where the added nucleotides can be labeled. The methods of the invention can involve the identification of a polynucleotide or polynucleotides having a contiguous non-redundant string or a superimposed non-redundant string pattern. The detection of the presence of a non-redundant contiguous string can be used, for example, to identify a particular gene. Alternatively, for example, if the non-redundant contiguous string is not unique to a particular gene, the string can be used to form a DNA library that can then be searched, for example, with a second string. Similarly, a superimposed non-redundant string pattern can be used, for example, to identify a gene or to search a DNA library. Such strings can be used, for example, in annealing reactions and in computer searches of a database having a catalog of sequenced polynucleotides.

28 Claims, No Drawings

```
                          SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (xi) SEQUENCE DESCRIPTION: SEQ ID NO:1:

GGGGG                                                               5

(2) INFORMATION FOR SEQ ID NO:2:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (xi) SEQUENCE DESCRIPTION: SEQ ID NO:2:

TACATGTACT GCT                                                      13

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (xi) SEQUENCE DESCRIPTION: SEQ ID NO:3:

TAACATGTAC TGCTT                                                    15

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (xi) SEQUENCE DESCRIPTION: SEQ ID NO:4:

ACATGTACTG CT                                                       12

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:5:

CATTAAAGGG AAAAGCCCAG TCA                                           23

(2) INFORMATION FOR SEQ ID NO:6:
```

-continued (i) SEQUENCE CHARACTERISTICS:
    (A) LENGTH: 13 base pairs
    (B) TYPE: nucleic acid
    (C) STRANDEDNESS: double
    (D) TOPOLOGY: linear (xi) SEQUENCE DESCRIPTION: SEQ ID NO:6:

CATAGAGCAG TCA                                                        13

SEQUENTIAL STEP METHOD FOR SEQUENCING AND IDENTIFYING POLYNUCLEOTIDES

This is a continuation of application Ser. No. 08/665,210 filed on Jun. 14, 1996, abandoned, which was filed concurrently with the following related U.S. patent applications: "Nuclease Protection Assays," R. Kumar, inventor, Ser. No. 08/665,104, U.S. Pat. No. 5,770,370; "Microfluidic Method for Nucleic Acid Amplification," Z. Loewy and R. Kumar, inventor, Ser. No. 08/665,209; "Method for Amplifying a Polynucleotide," Z. Loewy, inventor, Ser. No. 08/663,688; "Automated Nucleic Acid Preparation" D. Southgate and Z. Loewy, inventors, Ser. No. 08/664,780; and "Padlock Probe Detection," R. Kumar, inventor, Ser. No. 08/665,208. This patent application is related to the following copending U.S. patent applications: Ser. No. 60/009,517, filed Nov. 3, 1995; Ser. No. 60/006,202, filed Nov. 3, 1995; and Ser. No. 60/010,513, filed Jan. 24, 1996. All of the foregoing patent applications are hereby incorporated by reference herein in their entirety.

This invention was made with U.S. Government support under Contract No. 70NANB5H1037. The U.S. Government has certain rights in this invention.

In one aspect, the present invention provides a new method for determining the base sequence of RNA or DNA, termed sequential step sequencing. In another aspect, the present invention provides new methods of identifying a polynucleotide or polynucleotides using a contiguous string of non-redundant nucleotides or a superimposed non-redundant string pattern.

Prior art methods of sequencing include the Maxam-Gilbert method and the Sanger dideoxy method. In the Maxam-Gilbert method, a substrate DNA is labeled on one strand with $^{32}P$ at the 5'-hydroxyl terminus. The labeled DNA is then broken preferentially at one of the four nucleotides using one reaction mixture for each base, the reaction conditions causing an average of one break per DNA molecule. In the reaction mixture for each base, each broken chain yields a radiolabeled fragment extending from the $^{32}P$ 5'-hydroxyl terminus to one of the positions in the DNA in which that base appears. Thus, every time a base appears in a DNA molecule, it generates a fragment of a different size, which are then separated by gel electrophoresis. The autoradiogram of a gel in which all four chemical reactions have been entered into the gel shows a pattern of bands from which the sequence of the DNA can be read. See, for example, Stryer, *Biochemistry* (3d ed. 1988) at pages 120–121.

In the Sanger dideoxy method, DNA is sequenced by generating fragments through the controlled interruption of enzymatic replication. First, a primer is constructed which is complementary to the DNA sequence. Then, DNA polymerase is used to copy a sequence of a single-stranded DNA using the primer and four labeled deoxyribonucleoside triphosphates and a 2',3'-dideoxy analog of each of the triphosphates. The incorporation of an analog in the new DNA strand being synthesized results in the termination of incorporation of labeled deoxyribonucleoside triphosphates since the dideoxy analogs lack the 3'-hydroxyl terminus needed to form the next phosphodiester bond. Thus, the synthesis results in DNA fragments of various lengths in which the dideoxy analog is at the 3' end. The reaction mixture for each base can then be separately electrophoresed on a gel or electrophoresed together if the deoxyribonucleoside triphosphate corresponding to each base has a separate label. See, for example, Stryer, *Biochemistry* (3d ed. 1988) at pages 121–123.

The sequential step sequencing methods of the invention, unlike the above-described sequencing methods, involve individual reactions for each type of base in every position in which it appears on the DNA molecule, or for every position in which it appears next to a different type of base. The large number of reactions involved would likely have been considered impractical due to being too labor-intensive under the procedures known in the prior art for performing the necessary chemical reactions.

However, the sequential step sequencing methods of the invention can be used, for example, in the context of a microfluidics-based device for automatedly moving fluids in and out of a reaction chamber, which has been disclosed in U.S. patent Ser. No. 60/010,513, filed Jan. 24, 1996, the contents of which are incorporated herein by reference. This combination of the microfluidics-based system and the methods of the invention makes sequential step sequencing an attractive alternative to known conventional methods of nucleotide sequencing. Furthermore, the present invention provides an advantage in eliminating the need for electrophoresis, which is one of the most time-consuming steps of the sequencing reactions of the prior art. Additionally, the present invention provides for an increased rate of sequence read-out since nucleotide addition can occur, for example, at 800 nucleotides per minute.

Further, the present invention provides the advantage, for example, of providing a mechanism for more accurate determination of sequences, such as the sequence adjacent to the poly-A tail of a polynucleotide.

SUMMARY OF THE INVENTION

In one aspect, the present invention provides a method of sequential step sequencing of a polynucleotide having x number of nucleotides comprising:

(A) providing a single-stranded polynucleotide template and a first complementary primer having n nucleotides, wherein n is an integer greater than three;

(B) causing the template and the primer to anneal, thereby forming a template-primer complex;

(C) adding a template-dependent nucleotide polymerase and at least one nucleoside triphosphate or analog thereof having a label attached thereto, wherein the nucleoside triphosphate or analog thereof includes a base selected from the group consisting of adenine, thymine, cytosine, guanine, and uracil; and (D) determining whether a label is associated with the template-primer complex or which label is associated with the template-primer complex.

In preferred embodiments, the methods of the invention additionally include removing unincorporated nucleoside triphosphate or analog from the template-primer complex.

In certain embodiments of the above method, step (C) is limited to using one nucleoside triphosphate or analog thereof, further comprising:

if no label is associated with the template-primer complex as determined in step (D), then steps (A) to (D) are repeated using another nucleoside triphosphate or analog thereof having a different base than that used previously in step (C), steps (A) to (D) being repeated until it is determined that a label is associated with the template-primer complex.

Preferably, the method of claim 1 further comprises step (E), step (E) being, upon having determined which base was added to the first primer by exercise of step (D), a second primer is generated having n+y nucleotides, y being one or the number of identical adjacent nucleotides, wherein the added nucleotide or nucleotides are at its 3' end; and steps (A) to (D) are repeated with the proviso that the second primer is substituted for the first primer. Step (E) is preferably repeated until the primer is at least x nucleotides long, such that n=x.

In certain embodiments, the methods of the invention involve the use of a nucleoside triphosphate analog modified to preclude any subsequent addition of such analog after a first analog has been added to the primer. When such nucleoside triphosphate analog is used with the methods of the invention, in addition to adding one labeled nucleotide at a time, the methods also include the addition of more than one labeled nucleotide at a time. Thus, in certain embodiments, the nucleoside triphosphate analog of step (C) is a combination comprising two, three, or four different analogs having different bases, wherein the analogs having different bases are differentially labelled. Preferably, the differentially labeled analogs are labeled with fluorescent dyes. When a combination of two, three or four different analogs are used, it is preferred to use a combination of all four analogs in concert, the four analogs having the bases adenine, thymine, cytosine and guanine if the polymerase is DNA-dependent, or the bases adenine, uracil, cytosine and guanine if the polymerase is RNA-dependent.

The latter sequential step sequencing methods of the invention preferably include step (E), step (E) being, upon having determined which base was added to the first primer by exercise of steps (A) to (D), a second primer is generated having n+1 nucleotides, wherein the added nucleotide is at its 3' end; and steps (A) to (D) are repeated with the proviso that the second primer is substituted for the first primer. In certain preferred embodiments, step (E) is repeated until n is x nucleotides long, x being the number of nucleotides in the polynucleotide being sequenced, thereby providing for a full sequence.

In another aspect of the invention, the above-described methods of sequential step sequencing are used to sequence polynucleotides adjacent to a poly-A tail of the template, the methods further comprising the following steps prior to providing the first primer in step (A):

(a) providing a single-stranded polynucleotide template and an initial complementary primer, the template having a poly-A sequence, and the primer being a poly-T or a poly-U primer;

(b) causing the template and the primer to anneal, thereby forming a template-primer complex;

(c) adding a template-dependent nucleotide polymerase and a nucleoside triphosphate or analog thereof including a base, the base being thymine or uracil, thereby forming an elongated initial primer.

In certain embodiments, the sequenced polynucleotides near the poly-A tail of the template are contiguous, and optionally, the sequenced nucleotides form a non-redundant contiguous string. In other embodiments, the sequenced polynucleotides near the poly-A tail of the template are non-contiguous and form a superimposed non-redundant string pattern.

In certain embodiments, the first primer used in step (A) is the elongated initial primer, the primer being complementary to the 5' end of the poly-A sequence in the template polynucleotide. In other embodiments, the elongated initial primer is used to determine at least one nucleotide of the template adjacent to the poly-A sequence, and the first primer used in step (A) is complementary to this nucleotide and at least a portion of the poly-A sequence.

In the sequential step sequencing methods of the invention, the label attached to the nucleotide or nucleotide analog is preferably selected from the group consisting of a radioisotope, a fluorescent dye, a signal-generating enzyme, and a first ligand that specifically binds to a second ligand comprising a radioisotope, a fluorescent dye or a signal-generating enzyme, and most preferably, the label is a fluorescent dye, such as fluorescein or rhodamine.

In preferred embodiments of the methods of the invention, the template-primer complex is attached to a solid surface, such as a microparticle, which is preferably paramagnetic.

Further, in preferred embodiments, the template-dependent nucleotide polymerase is a DNA polymerase or an RNA polymerase or a fragment thereof having polymerase activity. Most preferably, the DNA polymerase or a fragment thereof having polymerase activity is T7 DNA polymerase, Klenow fragment of *E. coli* DNA polymerase I or Taq polymerase, and the RNA polymerase or a fragment thereof having polymerase activity are derived from *E. coli* or *S. cerevisiae*, for example.

Furthermore, the modified nucleoside triphosphate is preferably a dideoxynucleoside triphosphate.

In addition to providing sequential step sequencing, the present invention provides methods of identifying a polynucleotide or polynucleotides. One method of identifying a polynucleotide or polynucleotides comprises:

(A) providing a primer complementary to a contiguous string of non-redundant nucleotides, the primer having a label attached thereto;

(B) providing a single-stranded polynucleotide template;

(C) causing the template and the primer to anneal, thereby forming a template-primer complex;

(D) determining whether a label is associated with the template-primer complex or which label is associated with the template-primer complex.

Another method of identifying a polynucleotide or polynucleotides comprises:

(A) providing a base sequence of a string, the string being a superimposed non-redundant string pattern or a contiguous non-redundant string; and (B) searching a computer database of polynucleotide base sequences using the base sequence of the string. In embodiments wherein the string is a superimposed non-redundant string pattern, the above method preferably further comprises providing a computer program for searching for the superimposed string pattern in the polynucleotide sequences, the computer program being capable of identifying a superimposed string pattern despite the presence of a redundancy or redundancies within a sequence that includes the string pattern located in the polynucleotide or polynucleotides in the database.

DETAILED DESCRIPTION

DEFINITIONS

The following terms shall have the meaning set forth below:

sequential step sequencing—sequencing a polynucleotide by individual reactions, each reaction detecting no more than the sequence of one type of nucleotide at a time. The nucleotide detected can occur, for example, once or more than once in adjacent positions, such as G, GG or GGGGG (SEQ ID NO: 1).

actual non-redundant contiguous string—a base sequence in which the sequence of each base is actually not repeated in the immediately adjacent base. For example, TACATGTACTGCT (SEQ ID NO: 2) is an actual non-redundant contiguous string, whereas TA<u>ACATGTACTGCTT</u> (SEQ ID NO: 3) is not, although the underlined sequence within this sequence, ACATGTACTGCT (SEQ ID NO: 4), is an actual non-redundant contiguous string.

superimposed non-redundant string pattern—pattern derived from an actual sequence. In the pattern, the redundancies in the actual sequence are removed, a redundancy being the duplication of a base in the immediately adjacent base. For example, given an actual sequence CATTAAAGGGAAAAGCCAGTCA (SEQ ID NO: 5), the superimposed non-redundant string pattern of the sequence is CATAGAGCAGTCA (SEQ ID NO: 6).

In one aspect, the present invention relates to methods of sequencing of polynucleotides using sequential step sequencing. The sequential step sequencing methods of the invention, unlike the methods of the prior art, involve individual reactions for each type of base in every position in which it appears on the DNA molecule, or for every position in which it appears next to a different type of base. The methods of the invention are preferably used in the context of a microfluidics-based device for automatedly moving fluids in and out of a reaction chamber, which has been disclosed in U.S. patent Ser. No. 60/010,513, filed Jan. 24, 1996, the contents of which are incorporated herein by reference. The present invention provides an advantage over prior art methods, for example, in eliminating the need for electrophoresis, which is one of the most time-consuming steps of sequencing reactions. Additionally, the present invention provides for an increased rate of sequence readout since nucleotide addition can occur, for example, at 800 nucleotides per minute.

The methods of the invention begin with the provision of a single-stranded polynucleotide template that is annealed with a primer, forming a template-primer complex. In one aspect, the present invention provides for adding one nucleoside triphosphate or analog thereof at a time to the template-primer complex, the nucleoside triphosphate or analog being labelled. If necessary, each of the four nucleoside triphosphates or analogs is added until a label is detected due to the incorporation of a nucleotide into the complex. This method can be used with a nucleoside triphosphate analog that is modified to preclude any subsequent addition of such analog after a first analog has been added to the primer, such as a dideoxynucleoside triphosphate. Alternatively, this method can be used with a nucleoside triphosphate or analog thereof that does not stop addition after a first nucleotide or nucleotide analog has been added to the primer.

In other aspects of the invention, all four nucleoside triphosphates or analogs are added at once to the complex, each nucleoside triphosphate or analog having a different label. Using the latter method, the sequence at this position is determined by identifying the type of label incorporated into the complex. This method is preferably used only with a nucleoside triphosphate analog that is modified to preclude any subsequent addition of such analog after a first analog has been added to the primer.

In one aspect of the invention, when a nucleoside triphosphate or analog is used in the sequential step sequencing methods of the invention, in which the nucleoside triphosphate or analog is not modified to preclude any subsequent addition of such nucleoside triphosphate or analog after a first nucleotide has been added to the primer, the sequence obtained may not match the actual sequence of the polynucleotide. Instead, the sequence obtained may be a superimposed non-redundant string pattern. Specifically, if the polynucleotide sequence has a redundancy such that immediately adjacent bases are the same, the sequence obtained using the latter methods of the invention will only detect one of the bases. For example, a polynucleotide with a sequence of CATTAAAGGGAAAGCCCAGTCA (SEQ ID NO: 5) will be detected as the corresponding superimposed non-redundant string pattern, CATAGAGCAGTCA (SEQ ID NO: 6). Thus, in one aspect, the methods of the invention provide for the detection of a superimposed non-redundant string pattern in a polynucleotide template.

In another aspect of the invention, when a nucleoside triphosphate or analog is used in the sequential step sequencing methods of the invention, in which the nucleoside triphosphate or analog is not modified to preclude any subsequent addition of such nucleoside triphosphate or analog after a first nucleotide has been added to the primer, the sequence obtained will match the actual sequence of the polynucleotide when the amount of label attached to the nucleotide is quantified, using for example, autoradiography followed by scanning of the autoradiogram to determine signal strength.

More generally, in one aspect, the present invention provides a method of sequential step sequencing of a polynucleotide having x number of nucleotides comprising:

(A) providing a single-stranded polynucleotide template and a first complementary primer having n nucleotides, wherein n is an integer greater than three;

(B) causing the template and the primer to anneal, thereby forming a template-primer complex;

(C) adding a template-dependent nucleotide polymerase and at least one nucleoside triphosphate or analog thereof having a label attached thereto, wherein the nucleoside triphosphate or analog thereof includes a base selected from the group consisting of adenine, thymine, cytosine, guanine, and uracil;

(D) determining whether a label is associated with the template-primer complex or which label is associated with the template-primer complex.

Preferably, the above method also includes removing unincorporated nucleoside triphosphate or analog from the template-primer complex.

In certain embodiments of the above method, step (C) is limited to using one nucleoside triphosphate or analog thereof, and if no label is associated with the template-primer complex as determined in step (D), then steps (A) to (D) are repeated using another nucleoside triphosphate or analog thereof having a different base than that used previously in step (C), steps (A) to (D) being repeated until it is determined that a label is associated with the template-primer complex.

Preferably, the above methods further comprise step (E), step (E) being, upon having determined which base was added to the first primer by exercise of step (D), a second primer is generated having n+y nucleotides, y being one or the number of identical adjacent nucleotides, wherein the added nucleotide is at its 3' end; and steps (A) to (D) are repeated with the proviso that the second primer is substituted for the first primer. Step (E) is preferably repeated until the primer is at least x nucleotides long, such that n=x, n being the number of nucleotides in the polynucleotide being sequenced.

In certain embodiments, the methods of the invention involve the use of a nucleoside triphosphate analog modified to preclude any subsequent addition of such analog after a first analog has been added to the primer. When such nucleoside triphosphate analog is used with the methods of the invention, in addition to adding one labeled nucleoside triphosphate analog at a time, the methods also include the addition of more than one labeled nucleoside triphosphate analog at a time. Thus, in certain embodiments, the nucleoside triphosphate analog of step (C) is a combination comprising two, three, or four different nucleoside triphosphate analogs having different bases, wherein the nucleoside triphosphate analogs having different bases are differentially labeled. Preferably, the differentially labeled nucleoside triphosphate analogs are labeled with fluorescent dyes, such as fluorescein, rhodamine, 7-amino-4-methylcoumarin, dansyl chloride, Cy3, Hoechst 33258, R-phycoerythrin, Quantum Red™, Texas Red, suitable analogs and derivatives thereof, and the like, which can be obtained commercially, such as from Sigma.

When a combination of two, three or four different nucleoside triphosphate analogs are used, it is preferred to use a combination of all four different nucleoside triphosphate analogs are used in concert, the four nucleoside triphosphate analogs having the bases adenine, thymine, cytosine and guanine if the polymerase is DNA-dependent, or the bases adenine, uracil, cytosine and guanine if the polymerase is RNA-dependent.

The above-described sequential step sequencing methods of the invention preferably include step (E), step (E) being, upon having determined which base was added to the first primer by exercise of steps (A) to (D), a second primer is generated having n+1 nucleotides, wherein the added nucleotide or nucleotides are at its 3' end; and steps (A) to (D) are repeated with the proviso that the second primer is substituted for the first primer. In certain preferred embodiments, step (E) is repeated until n is x nucleotides long, x being the number of nucleotides in the polynucleotide being sequenced, thereby providing for a full sequence.

The methods of the present invention can be used, for example, to sequence the 3' end of an mRNA or a cDNA nucleotide sequence. Using sequential step DNA sequencing and a poly-T or a poly-U primer, nucleoside triphosphates or analogs thereof having the bases thymine or uracil are added until the primer is extended to the beginning of the poly-A tail. The sequence from this point is then determined using the methods of sequential step sequencing described above, and can be used to determine the actual sequence, or a superimposed non-redundant string pattern. This aspect of the invention overcomes the problems associated with the prior art sequencing methods, such as the presence of a smear on the sequencing gel since a poly-T or poly-U primer randomly anneals to different parts of the poly-A tail.

Specifically, the above-described methods of sequential step sequencing can be used to sequence polynucleotides adjacent to a poly-A tail of the template, the methods further comprising the following steps prior to providing the first primer in step (A):

(a) providing a single-stranded polynucleotide template and an initial complementary primer, the template having a poly-A sequence, and the primer being a poly-T or a poly-U primer;

(b) causing the template and the primer to anneal, thereby forming a template-primer complex;

(c) adding a template-dependent nucleotide polymerase and a nucleoside triphosphate or analog thereof including a base, the base being thymine or uracil, thereby forming an elongated initial primer.

In certain embodiments, the sequenced polynucleotides near the poly-A tail of the template are contiguous, and optionally, the sequenced nucleotides form a non-redundant contiguous string. In other embodiments, the sequenced polynucleotides near the poly-A tail of the template are non-contiguous and form a superimposed non-redundant string pattern.

In certain embodiments, the first primer used in step (A) is the elongated initial primer, the primer being complementary to the 5' end of the poly-A sequence in the template polynucleotide. In other embodiments, the elongated initial primer is used to determine at least one nucleotide of the template adjacent to the poly-A sequence, and the first primer used in step (A) is complementary to this nucleotide and at least a portion of the poly-A sequence.

Preferably, the primers used in the methods of the invention are about 10 to about 50 nucleotides long, and more preferably, about 15 to about 30 nucleotides long.

In preferred embodiments of the sequencing methods of the invention, the label attached to the nucleoside triphosphate or analog is preferably selected from the group consisting of a radioisotope, a fluorescent dye, a signal-generating enzyme, and a first ligand that specifically binds to a second ligand comprising a radioisotope, a fluorescent dye or a signal-generating enzyme, and most preferably, the label is a fluorescent dye. Suitable radioisotopes include, but are not limited to, $^{3}H$, $^{14}C$, and $^{32}P$. Suitable fluorescent dyes include, but are not limited to, fluorescein, rhodamine, 7-amino-4-methylcoumarin, dansyl chloride, Cy3, Hoechst 33258, R-phycoerythrin, Quantum Red™, Texas Red, suitable analogs and derivatives thereof, and the like. Suitable signal-generating enzymes include, but are not limited to, alkaline phosphatase, peroxidase, and urease. Any of the aforementioned labels can be obtained commercially, such as from Sigma.

For instance, labeling methods are described in: Sinha and Striepeke, "Oligonucleotides with Reporter Groups Attached to the 5' Terminus" in Oligonucleotides and Analogues: A Practical Approach, Eckstein, Ed., IRL, Oxford, 1991, p. 185 et seq.; Sinha and Cook, "The Preparation and Application of Functionalized Synthetic Oligonucleotides: 3. Use of H-Phosphate Derivatives of Protected Amino-Hexanol and Mercapto-Propanol or Mercapto-Hexanol," Nucleic Acids Research, 1988, Vol. 16, p. 2659 et seq.; Haugland, Molecular Probes Handbook of Fluorescent Probes and Research Chemicals, Molecular Probes, Inc., Eugene, Oreg., 1992, p. 20 et seq.; Theisen et al., "Fluorescent Dye Phosphoramidite Labelling of Oligonucleotides," Tetrahedron Letters, 1992, Vol. 33, p. 3036 et seq.; Rosenthal and Jones, "Genomic Walking and Sequencing by Oligocassette Mediated Polymerase Chain Reaction," Nucleic Acids Research, 1990, Vol. 18, p. 3095 et seq.; Smith et al., "The Synthesis of Oligonucleotides containing an Aliphatic Amino Group at the 5' Terminus—Synthesis of Fluorescent DNA Primers for Use in DNA-Sequence Analysis," Nucleic Acids Research, 1985, Vol. 13, 2399 et seq.

The detection used in conjunction with the invention will depend on the nature of the label. Where a colorimetric or fluorescent label is used visual inspection or an optical instrument such as the fluorescence microscope from Olympus (Lake Success, N.Y.), the Plate Reader device from BioTek Instruments (Winooski, Vt.) and the CCD (charge-coupled device) camera from Princeton Instruments (Princeton, N.J.). Where radioisotopes are used, detection can comprise such spatially sensitive detection devices as the Phosphor Imager device (Molecular Dynamics, Sunnyvale, Calif.), or can comprise separately detecting individual solid surfaces in a detection apparatus such as a gamma-counter or a liquid scintillation counter.

Further, the template-primer complex is preferably attached to a solid surface, such as a microparticle, which is preferably paramagnetic. A microparticle can have any shape, and preferably it is spherical. Preferably, it has a diameter of less than 1 mm, and more preferably, less than 500 microns. In certain prefererred embodiments, the microparticles have a diameter from about 0.5 micron to about 25 microns, and more preferably about 1 micron to about 5 microns, and even more preferably, about 2 microns to about 4 microns. Microparticles are comprised of any suitable material, the choice of material being guided by its characteristics, which preferably include minimal non-specific absorptive characteristics, such as that of polystyrene. In other embodiments, the microparticles are comprised of, for example, plastic, glass, cellulose, a cellulose derivative, nylon, polytetrafluoroethylene ("TEFLON"), ceramic and the like. A paramagnetic bead can be comprised of, for example, iron dispersed in a polystyrene matrix. A paramagnetic bead can be comprised of, for example, iron dispersed in a polystyrene matrix, and can be obtained with an associated biomolecule, for example, from Dynal (Oslo, Norway), or without an associated biomolecule, for example, from Bang Laboratories (Carmel, Ind.).

Additionally, in preferred embodiments, the template-dependent nucleotide polymerase is a DNA polymerase or an RNA polymerase or a fragment thereof having polymerase activity. Most preferably, the DNA polymerase or a fragment thereof having polymerase activity is T7 DNA polymerase, the Klenow fragment of *E.coli* DNA polymerase I or Taq polymerase and the RNA polymerase or a fragment thereof having polymerase activity is derived from *E.coli* or *S.cerevisiae*.

Furthermore, the modified nucleoside triphosphate is preferably a dideoxynucleoside triphosphate. Reaction conditions for the methods of the invention can be found, for example, in EP 0 223 618 and Maniatis et al., *Molecular Cloning* (Cold Spring Harbor 1982) which are hereby incorporated by reference herein in their entirety. Additionally, where methodologies are referred to herein without specific enumeration of well-known methods steps, generally, the following text can be referenced for further details: Ausubel et al., *Short Protocols in Molecular Biology*; Sambrook et al., *DNA Cloning, A Laboratory Manual*; and *Molecular Biology Protocols*, web-site: listeria.nwfsc.noaa.gov/protocols.html.

In preferred embodiments, the methods of the invention are used in the context of a microfluidics-based device for automatedly moving fluids in and out of a reaction chamber, which has been disclosed in U.S. patent Ser. No. 60/010,513, filed Jan. 24, 1996, the contents of which are incorporated herein by reference. The microfluidics device is designed specifically for moving small volumes of fluids through fluid exchange channels that connect various sorts of fluid chambers. In particular, such a device comprises a fluid chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the device includes a reaction chamber. The reaction chamber is comprised of any suitable material, as are all fluid chambers, such as, for example, glass, plastic, ceramic, or combinations thereof, and is connected to at least two fluid exchange channels for passaging material in and out of the reaction chamber. The reaction chamber preferably remains at a constant temperature of within about two degrees centigrade, wherein the temperature is between about 20° C. and 65° C., and alternatively can have adjustable temperatures as in accordance with the requisites of the reactions to take place therein.

The liquid distribution system can conduct synthesis in a great number of separate reaction wells, such as 10,000 reaction wells. The synthesis in each reaction well can occur on a bead or microparticle or can occur on the surfaces of the wells, where these surfaces have been appropriately treated. The wells are formed on a plate that is separable from the portions of the liquid distribution system used to shuttle reagents to a multitude of reaction wells. Another way of forming an array is to apply the photolithographic synthesis procedures described in a number of patents and patent applications owned by Affymax, Inc. These include Fodor et al., "Very Large Scale Immobilized Polymer Synthesis," WO92/10092; Dovor et al., "Method of Synthesizing Diverse Collections of Oligomers," WO93/06121; Campbell et al., "Methods for Synthesis of Phosphonate Esters," U.S. Pat. No. 5,359,115; Campbell, "Methods for Synthesis of Phosphonate Esters," U.S. Pat. No. 5,420,328; Fodor et al., "Very Large Scale Immobilized Polymer Synthesis," U.S. Pat. No. 5,424,186; and Pirrung et al., "Large Scale Photolithographic Solid Phase Synthesis of Polypeptides and Receptor Binding Screening Thereof," U.S. Pat. No. 5,143,854.

In another aspect, the methods of the invention involve the identification of a polynucleotide or polynucleotides having a contiguous non-redundant string or a superimposed non-redundant string pattern. The detection of the presence of a non-redundant contiguous string can be used, for example, to identify a particular gene. Alternatively, for example, if the non-redundant contiguous string is not unique to a particular gene, the string can be used to form a DNA library that can then be searched, for example, with a second string. Similarly, a superimposed non-redundant string pattern can be used, for example, to identify a gene or to search a DNA library. Preferably the string is at least about 10 nucleotides long, and more preferably, the string is at least about 12 nucleotides long.

Specifically, one method of identifying a polynucleotide or a group of nucleotides, comprises:

(A) providing a primer complementary to a contiguous string of non-redundant nucleotides, said primer having a label attached thereto;

(B) providing a single-stranded polynucleotide template;

(C) causing the template and the primer to anneal, thereby forming a template-primer complex;

(D) determining whether a label is associated with the template-primer complex or which label is associated with the template-primer complex.

Another method of identifying a polynucleotide or a group of polynucleotides comprises:

(A) providing a base sequence of a string, the string being a superimposed non-redundant string pattern or a contiguous non-redundant string; and (B) searching a computer database of polynucleotide base sequences using the base sequence of the string. In embodiments wherein the string is a superimposed non-redundant string pattern, the above method preferably further comprises providing a computer program for searching for the superimposed string pattern in the polynucleotide sequences, the computer program being capable of identifying a superimposed string pattern despite the presence of a redundancy or redundancies within a sequence that includes the string pattern located in the base sequence of a polynucleotide or polynucleotides in the database.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed:

1. A method of sequential step sequencing of a polynucleotide sequence with two or more iterations of steps (A) through (E) below, wherein the polynucleotide sequence is included on a polynucleotide template, the method comprising:
   (A) providing the polynucleotide template and a first primer, wherein the first primer has at least three nucleotides and is complementary to a segment of the polynucleotide template;
   (B) causing the template and the first primer to anneal, thereby forming a template-primer complex;
   (C) adding a template-dependent nucleotide polymerase and at least one nucleoside triphosphate or analog thereof having a label attached thereto, wherein each nucleoside triphosphate or analog thereof includes a base selected from the group consisting of adenine, thymine, cytosine, guanine, and uracil;
   (D) detecting a signal from any label incorporated into the template-primer complex;
   (E) if no label is incorporated into the template-primer complex as determined in step (D), then steps (C) and (D) are repeated using another nucleoside triphosphate or analog thereof having a different base than that used previously in step (C), steps (C) and (D) being repeated until it is determined that the label is incorporated into the template-primer complex, thereby identifying which nucleoside triphosphate was added to the 3' end of the primer; and
   (F) generating a new primer having at least three nucleotides that includes a base or bases identified in the immediately preceding iteration of steps (A) through (E) at the new primer's 3' end, wherein the nucleotide at the 3' end of the new primer does not have a label attached thereto; and steps (A) to (E) are repeated with the proviso that the new primer is substituted for the first primer.

2. The method of claim 1, further comprising removing unincorporated nucleoside triphosphate from the template-primer complex.

3. The method of claim 1, wherein the method in step (C) employs a combination comprising nucleoside triphosphates or analogs which include two, three, or four different bases which are differentially labeled.

4. The method of claim 3, wherein the differentially labeled analogs are labeled with fluorescent dyes.

5. The method of claim 3, wherein four different nucleoside triphosphates or analogs are used in concert, the four nucleoside triphosphates or analogs having the bases adenine, thymine, cytosine and guanine if the polymerase is DNA-dependent, or the bases adenine, uracil, cytosine and guanine if the polymerase is RNA-dependent.

6. The method of claim 1, wherein the method includes sequencing of polynucleotides adjacent to a poly-A segment of the template, wherein the first primer comprises poly-T or poly-U.

7. The method of claim 6, wherein the first primer is used to determine at least one nucleotide of the template adjacent to the poly-A segment.

8. The method of claim 1, wherein the label is selected from the group consisting of a radioisotope, a fluorescent dye, a signal-generating enzyme, and a first ligand that specifically binds to a second ligand comprising a radioisotope, a fluorescent dye or a signal-generating enzyme.

9. The method of claim 8, wherein the label is a fluorescent dye.

10. The method of claim 9, wherein the fluorescent dye is fluorescein or rhodamine.

11. The method of claim 1, wherein the template-primer complex is attached to a solid surface.

12. The method of claim 11, wherein the solid surface is a microparticle.

13. The method of claim 12, wherein the microparticle is paramagnetic.

14. The method of claim 1, wherein the template-dependent nucleotide polymerase is a DNA polymerase or an RNA polymerase or a fragment thereof having polymerase activity.

15. The method of claim 14, wherein the DNA polymerase or a fragment thereof having polymerase activity is T7 DNA polymerase, Klenow fragment of *E.coli* Polymerase I or Taq polymerase.

16. The method of claim 14, wherein the RNA polymerase or a fragment thereof having polymerase activity is derived from *E.coli* or *S. cerevisiae*.

17. The method of claim 1, wherein the nucleotide analog is a dideoxynucleoside triphosphate.

18. A method of identifying a polynucleotide by searching a database, comprising:
    (A) providing a nucleotide sequence of the polynucleotide to be identified;
    (B) determining a search string, the search string being a superimposed or contiguous non-redundant string pattern based on the nucleotide sequence; and
    (C) computer searching a computer database of known polynucleotide base sequences to identify superimposed or contiguous non-redundant string patterns matching the search string.

19. The method of claim 18, wherein the search string is a superimposed non-redundant string, the method further comprising:
    (D) providing a computer program for searching for the search string in the polynucleotide sequences, the computer program being capable of identifying a superimposed string pattern despite the presence of a redundancy or redundancies within a sequence that includes the string pattern located in the polynucleotide or polynucleotides in the database.

20. A method of sequential step sequencing for identifying a superimposed non-redundant string pattern in a polynucleotide sequence having contiguous redundant nucleotides, wherein the polynucleotide sequence is included in a polynucleotide template, comprising:

(A) providing the polynucleotide template and a first primer, wherein the first primer has at least three nucleotides and is complementary to a segment of the polynucleotide template;

(B) causing the template and the first primer to anneal, thereby forming a template-primer complex;

(C) adding a template-dependent nucleotide polymerase and at least one nucleoside triphosphate or analog thereof having a label attached thereto, wherein each nucleoside triphosphate or analog thereof includes a base selected from the group consisting of adenine, thymine, cytosine, guanine, and uracil;

(D) detecting a signal from any label incorporated into the template-primer complex;

(E) if no label is incorporated into the template-primer complex as determined in step (D), then steps (C) and (D) are repeated using another nucleoside triphosphate or analog thereof having a different base than that used previously in step (C), steps (C) and (D) being repeated until it is determined that the label is incorporated into the template-primer complex, thereby identifying which base was added to the primer, which identifies the next base of the superimposed non-redundant string pattern; and (F) generating a new primer having at least three nucleotides that includes the identified base of step (C) or (E) at the new primer's 3' end, which identified base is included in as many contiguous nucleotides as the identified base's complement in the polynucleotide sequence, wherein the nucleotide at the 3' end of the new primer is extendable; and steps (A) to (E) are repeated with the proviso that said new primer is substituted for the first primer.

21. The method of claim 20, further comprising removing unincorporated nucleotide triphosphates from the template-primer complex.

22. The method of claim 20, wherein the method includes sequencing of a superimposed non-redundant string pattern adjacent to a poly-A segment on the template, wherein the first primer comprises poly-T or poly-U.

23. The method of claim 20, wherein the template-primer complex is attached to a solid surface.

24. The method of claim 23, wherein the solid surface is a paramagnetic microparticle.

25. The method of claim 1, wherein the new primer is generated by a DNA polymerase.

26. The method of claim 20, wherein the new primer is generated by a DNA polymerase.

27. The method of claim 1, wherein at each iteration, the new primer incorporates a single newly identified base.

28. The method of claim 1, wherein the signal from the label incorporated into the template-primer complex is quantified.

* * * * *